United States Patent [19]

Klaubert

[11] Patent Number: 4,461,900
[45] Date of Patent: Jul. 24, 1984

[54] 4,5-DIHYDROTHIADIAZOLE 1,1-DIOXIDE DERIVATIVES

[75] Inventor: Dieter H. Klaubert, Flemington, N.J.

[73] Assignee: American Home Products Corporation, New York, N.Y.

[21] Appl. No.: 474,908

[22] Filed: Mar. 14, 1983

[51] Int. Cl.³ .................. C07D 417/12; C07D 417/14
[52] U.S. Cl. .................... 546/209; 548/128; 546/277; 424/267; 424/263; 424/270
[58] Field of Search .............. 546/209; 548/128

[56] References Cited

FOREIGN PATENT DOCUMENTS

| 40696 | 12/1981 | European Pat. Off. | 348/135 |
| 7124646 | 1/1973 | France | 548/128 |
| 8004967 | 3/1981 | Netherlands | 548/135 |

OTHER PUBLICATIONS

Lawson et al., "Synthesis and Ring Closure of some Iodomethylsulphonyl-Benzamidines and Guanidines," J. Chem. Soc. (C) 1429 (1970).
Etienne et al., "Synthèse de Dérivés Substitués en 3 et 4 Par Cyclisation Acylante de Chlorométhylsulfonyliso-Urées et Iso-Thio-Urées," Bull. Soc. Chim., France, 1580 (1974).
Annual Reports in Medicinal Chemistry, pp. 83-86, (1981).

Primary Examiner—Robert T. Bond
Attorney, Agent, or Firm—Richard K. Jackson

[57] ABSTRACT

The compound of formula:

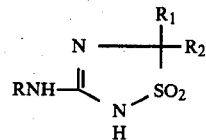

where
$R_1$ and $R_2$ are hydrogen or alkyl;
R is

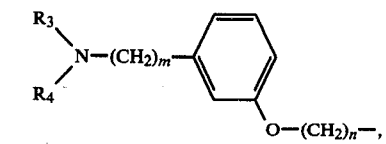

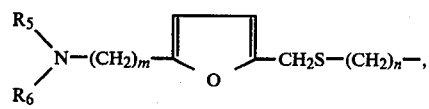

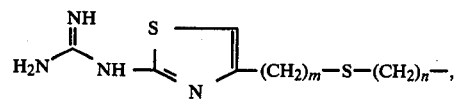

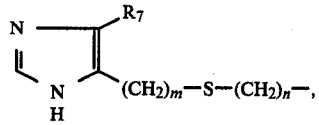

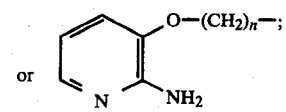

$R_3$ and $R_4$ are hydrogen, alkyl or alkylene;
$R_5$ and $R_6$ are hydrogen, alkyl or alkylene;
m is 1 to 6 and n is 2 to 6; and,
$R_7$ is hydrogen or alkyl;

or a pharmaceutically acceptable salt thereof, are $H_2$-receptor antagonists useful in the treatment of peptic ulcer disease.

2 Claims, No Drawings

4,5-DIHYDROTHIADIAZOLE 1,1-DIOXIDE DERIVATIVES

BACKGROUND OF THE INVENTION

Of the first generation H₂-receptor blockers useful in the treatment of peptic ulcer disease, the best known is cimetidine which presents the structural formula:

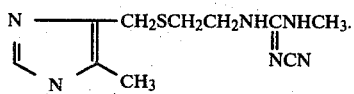

Ranitidine

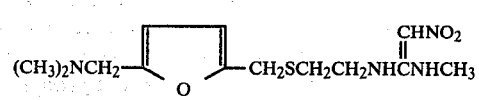

is about 5 times as potent as cimetidine in blocking histamine induced gastric acid secretion in the dog and between 5 and 10 times as potent as cimetidine in suppressing pentagastrin induced gastric acid secretion. Tiotidine

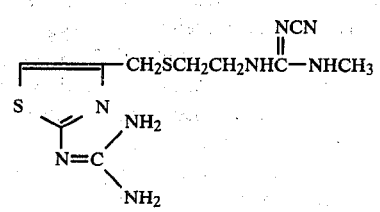

is reportedly at least ten times as potent as cimetidine in both in vitro and in vivo studies of H₂ receptor antagonism.
Etintidine

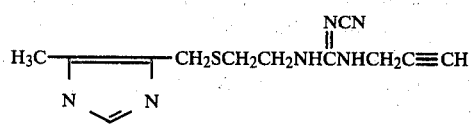

differs from cimetidine in the N-propargyl substituent and is more potent than cimetidine as an H₂-receptor antagonist. Etintidine possesses some anticholinergic activity. Thus, both potency and selectivity of H₂-receptor antagonism activity varies with modification of the structure of cimetidine.

DESCRIPTION OF THE INVENTION

In accordance with this invention there is provided a group of anti-secretory agents which act as H₂-receptor antagonists useful in the treatment of peptic ulcer disease, of the formula:

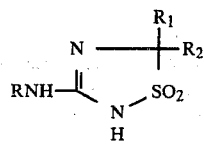

in which

R₁ and R₂ are, independently, hydrogen or alkyl of 1 to 6 carbon atoms;

R is

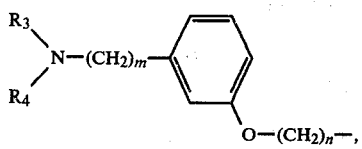

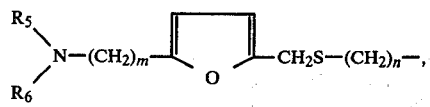

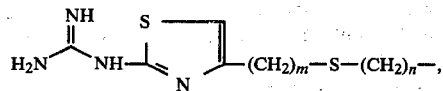

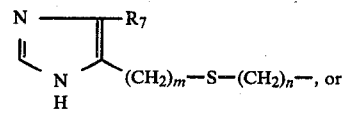

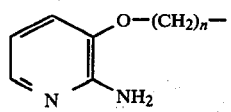

where

R₃ and R₄ are, independently, hydrogen or alkyl of 1 to 6 carbon atoms and when taken together, alkylene of 3 to 7 carbon atoms;

R₅ and R₆ are, independently, hydrogen or alkyl of 1 to 6 carbon atoms and when taken together, alkylene of 3 to 7 carbon atoms;

m is one of the integers 1, 2, 3, 4, 5 or 6;

n is one of the integers 2, 3, 4, 5 or 6; and

R₇ is hydrogen or alkyl of 1 to 6 carbon atoms;

or a pharmaceutically acceptable salt thereof.

The pharmaceutically acceptable salts of the compounds of this invention are produced from inorganic or organic acids such as hydrochloric, hydrobromic, sulfuric, phosphoric, nitric, formic, acetic, propionic, oxalic, succinic, glycollic, lactic, malic, tartaric, citric, ascorbic, maleic, phenylacetic, benzoic, para-amino-benzoic, salicylic, methanesulfonic acid, and the like.

Each of the amino substituents of the 4,5-dihydrothiadiazole 1,1-dioxide in their preferred scope are described in the following subgeneric descriptions of the invention.

(A) A compound of the formula

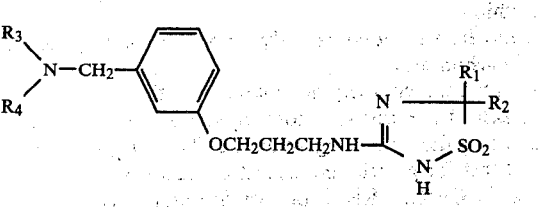

in which

R₁ and R₂ are, independently, hydrogen or alkyl of 1 to 6 carbon atoms; and $R_3$ and $R_4$ are, independently, hydrogen or alkyl of 1 to 6 carbon atoms and when taken together, alkylene of 3 to 7 carbon atoms;

or a pharmaceutically acceptable salt thereof.

(B) A compound of the formula

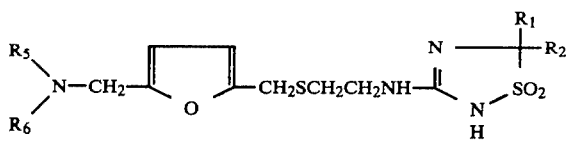

in which $R_1$ and $R_2$ are, independently, hydrogen or alkyl of 1 to 6 carbon atoms; and $R_5$ and $R_6$ are, independently, hydrogen or alkyl of 1 to 6 carbon atoms and when taken together, alkylene of 3 to 7 carbon atoms;

or a pharmaceutically acceptable salt thereof.

(C) A compound of the formula

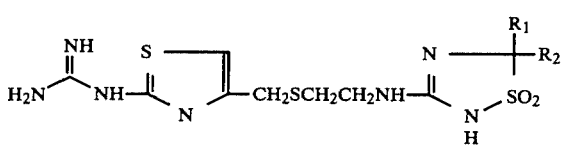

in which $R_1$ and $R_2$ are, independently, hydrogen or alkyl of 1 to 6 carbon atoms;

or a pharmaceutically acceptable salt thereof.

(D) A compound of the formula

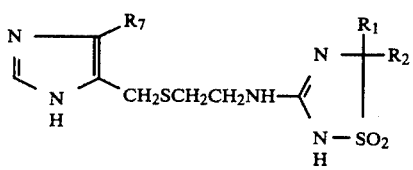

in which $R_1$ and $R_2$ are, independently, hydrogen or alkyl of 1 to 6 carbon atoms; and $R_7$ is hydrogen or alkyl of 1 to 6 carbon atoms;

or a pharmaceutically acceptable salt thereof.

(E) A compound of the formula

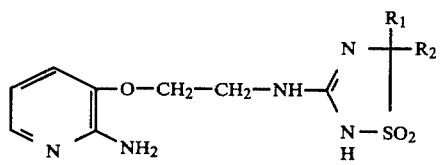

in which $R_1$ and $R_2$ are, independently, hydrogen or alkyl of 1 to 6 carbon atoms;

or a pharmaceutically acceptable salt thereof.

Each of the anti-secretory agents of this invention is active in the following scientifically recognized, standard test for gastric anti-secretory activity:

Male Charles River rats of Sprague-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally (i.d.), 37 mg/kg, immediately after ligation. The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1N NaOH. The calculated product of gastric volume (ml/4 hr) and acid concentration mEq/L estimates the total acid output (TAO, mEq/4 hr) over the four-hour test period. An analysis of variance is performed on these data to determine statistically significant ($p<0.05$) deviation between control versus drug-treated groups.

In addition, the compounds were tested in vitro by the following procedure:

The right atria of Males Charles River guinea-pigs (250-325 gm), trimmed of extraneous tissues is suspended in a bath at a 1.0 g tension load between an anchor and a Grass Model FT03 force displacement transducer which is coupled to a Beckman Dynograph recorder. The Krebs-Henseleit bath is oxygenated (95% $O_2$-5% $CO_2$) and maintained at 32° C. After establishing a regular pattern of spontaneous activity over one hour, cumulative doses of histamine are introduced into the bath and the maximal heart rate increase recorded after each addition to establish a response control.

Then the tissue is washed, returned to rest rates and the compound being treated is introduced into the bath. Thirty minutes later the histamine dose-response study is repeated. The response to histamine in the presence of an antagonist differs from that obtained in the absence of antagonist and the log of the ratio of differences is platted against the log concentration of antagonist for each of several concentrations from which the apparent dissociation constant ($pA_2$) is calculated. Cimetidine is employed as a standard. Its $pA_2$ (95% interval) value is 6.40 (6.62-6.17).

The compounds of this invention are prepared by the reaction of the amine $RNH_2$ with 4-carbethoxy-3-methylmercapto-4,5-dihydrothiazole 1,1-dioxide. Surprisingly, the reaction proceeds smoothly, with elimination of the carbethoxy group and no extensive ring degradation. It was discovered that, contrary to the instruction of Etienne et al., Bull. Soc. Chim. France, pp. 1580-1584 (1974) and French Pat. No. 2,145,005, displacement of the ethoxycarbonyl substituent proceeds without excessive ring degradation if the reaction is permitted to proceed at ambient temperature for an extended period of time ca 1 to 4 days. It is preferred that an excess of the amine reactant, even up to as much as four equivalents, be employed during the reaction although a stoichiometric amount is sufficient.

The following examples illustrate the process employed in production of the compounds of this invention. The in vitro and in vivo data for $H_2$ antagonism and activity at 32 mg/kg, respectively, presented in the examples is representative of all the compounds of invention.

EXAMPLE 1

N-[2-[[[5-[(DIMETHYLAMINO)METHYL]-2-FURANYL]METHYL]THIO]ETHYL]-4,5-DIHYDRO-1,2,4-THIADIAZOL-3-AMINE 1,1-DIOXIDE

A mixture of 2.38 g (10 mmol) of 4-carbethoxy-3-methylmercapto-4,5-dihydrothiadiazole-1,1-dioxide and 2.14 g (10 mmol) of 5-(2-aminoethylmercaptomethyl)-2-dimethylaminomethyl furan in 125 ml of methanol is stirred for 2 days at room temperature. The reaction mixture is evaporated to dryness and chromatographed on silica gel (25% MeOH—$CH_2Cl_2$) to obtain an oil which is dissolved in ethanol and oxalic acid is added. The resultant crystalline product is collected to provide the title compound as the ethanedioate; 1.2 g, mp 138°–139° C.

Analysis for: $C_{12}H_{20}N_4O_3S_2 \cdot C_2H_2O_4$: Calculated: C, 39.80; H, 5.25; N, 13.27. Found: C, 39.64; H, 5.37; N, 13.59.

$H_2$ antagonism active at $10^{-4}$, $10^{-5}$M.

EXAMPLE 2

4,5-DIHYDRO-N-[3-[3-[(1-PIPERIDINYL)METHYL]PHENOXY]PROPYL]-1,2,4-THIADIAZOL-3-AMINE 1,1-DIOXIDE

Substituting 3(3-piperidinylmethylphenoxy)propylamine in the method of Example 1 and allowing the reaction to stir for 4 days gives an oil after evaporation that is treated with oxalic acid in ethanol. The resulting gum is triturated with diethyl ether to give the crystalline product, mp 93° C.(dec) as an ethanedioate, hemiethanolate.

Analysis for: $C_{17}H_{26}N_{24}SO_3 \cdot C_2H_2O_4 \cdot \frac{1}{2}EtOH$: Calculated: C, 50.08; H, 6.51; N, 11.68. Found: C, 49.72; H, 6.85; N, 12.05.

$H_2$ antagonism $2 \times 10^{-7}$.

EXAMPLE 3

N-[2-[[[5-METHYL-2-IMIDAZOLYL]METHYL]THIO]ETHYL]-4,5-DIHYDRO-1,2,4-THIADIAZOL-3-AMINE 1,1-DIOXIDE 3-(Aminoethylthiomethyl)-4-methyl-imidazole (3.33 g; 10 mmol) is added to 50 ml methanol containing 18.6 ml of 1.08N $NaOCH_3$ in methanol. The solution is stirred for 15 minutes and evaporated to dryness. The residue is extracted with $CH_2Cl_2$ and evaporated to dryness. The residue is taken up in 50 ml methanol and 2.38 g (10 mmol) of 4-carbethoxy-3-methylmercapto-4,5-dihydrothiadiazole-1,1-dioxide is added. The solution is stirred over night. Thin layer chromatography is used to follow the course of the reaction. After one day, TLC demonstrated the presence of very little starting material. The reaction is permitted to continue for two additional days to guarantee removal of the —$CO_2Et$ group and then the solution is taken to dryness, dissolved in ethanol, filtered and to the filtrate 1.2 g oxalic acid in ethanol is added to precipitate the product. The product is filtered, washed with ethanol and diethylether to yield the title compound as the oxalate, still partially contaminated with the N-ethoxycarbonyl containing product and some ethanol as indicated by infrared and nuclear magnetic resonance analysis.

Thus, the compounds of this invention are useful in the treatment of peptic ulcer disease by virtue of their $H_2$-receptor antagonistic properties which provide antisecretory activity.

The dosage regimen for therapeutic use of the antisecretory agents disclosed herein will vary with the mode of administration, size and age of the person under treatment as well as the severity of the dysfunction. Therefore, treatment of peptic ulcer disease must be individualized for the patient under the guidance of the attending physician.

The compounds of this invention may be administered by conventional oral or parenteral routes as solids, liquids or isotonic solutions. Conventional adjuvants known to the art may be combined with the compounds disclosed herein to provide compositions and solutions for administration purposes although it is considered desirable and feasible to use the compounds neat or pure without additives other than for the purpose of providing suitable pharmaceutically acceptable solid or liquid dosage unit forms.

Based upon their potency relative to cimetidine, introductory dosage will be about or somewhat less than that of cimetidine by the same routes and modes of administration.

What is claimed is:

1. A compound of the formula:

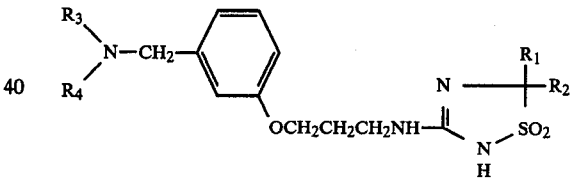

in which $R_1$ and $R_2$ are, independently, hydrogen or alkyl of 1 to 6 carbon atoms; and $R_3$ and $R_4$ are, independently, hydrogen or alkyl of 1 to 6 carbon atoms and when taken together, alkylene of 3 to 7 carbon atoms;

or a pharmaceutically acceptable salt thereof.

2. The compound of claim 1 which is 4,5-dihydro-N-[3-[3-[(1-piperidinyl)methyl]phenoxy]propyl]-1,2,4-thiadiazol-3-amine 1,1-dioxide or a pharmaceutically acceptable salt thereof.

* * * * *